United States Patent

Correa et al.

Patent Number: 5,882,203
Date of Patent: Mar. 16, 1999

[54] METHOD OF DETECTING DEPRESSION

[76] Inventors: Elsa I. Correa, 11726 Greenspring Ave., Lutherville, Md. 21093; Christina Barrett Barrick, 305 Chestnut Glen Garth, Towson, Md. 21204

[21] Appl. No.: 456,031

[22] Filed: May 31, 1995

[51] Int. Cl.$^6$ .................................................. G09B 19/00
[52] U.S. Cl. ........................................ 434/236; 434/238
[58] Field of Search .................................. 434/236–238, 434/322–323, 363

[56] References Cited

U.S. PATENT DOCUMENTS 4,627,818  12/1986  Von Fellenberg ....................... 434/236
5,195,033   3/1993  Samph et al. ........................... 434/323

OTHER PUBLICATIONS

Cohen E;Hunter I; Severity of Depression Differentiated by a Color Selection Test, American Journal of Psychiatry (Title Only), May 1978.

*Primary Examiner*—Kien T. Nguyen
*Assistant Examiner*—John Edmund Rovnak
*Attorney, Agent, or Firm*—Max Stul Oppenheimer

[57] ABSTRACT

The present invention relates to a method of detecting depression and its severity. A series of statements formulated to detect the presence and severity of depression are presented to the subject in a multiple item visual analog format. The subject's answers are given a numerical value. The total score is then normatively ranked to determine the presence and severity of the depression.

4 Claims, 3 Drawing Sheets

CORREA – BARRICK SCALE
Clinical Rating for Depression not at all — very much

1. My daily activities are smooth and effortless.
2. I have sleep problems: trouble falling asleep/interrupted sleep/awaken too early/sleeping too much.
3. I look forward to fun things (hobbies/interests/social contact) as much as I usually do.
4. I feel too tired to get through my regular day or need naps more often.
5. My body feels "heavy" (slowed down, sluggish, tired).
6. My concentration is as good as ever.
7. I feel restless/tense/anxious/jittery/wring my hands.
8. I think there is something wrong with my health.
9. My interest in being sensual/physical/loving is the same.
10. I notice that everything seems gray/cloudy/drab/lacking color.
11. I feel depressed (sad, blue, and gloomy).
12. I feel calm/relaxed/easy-going with people.
13. I brood and worry a lot (think about the same thing over and over again).
14. I have more personal faults and shortcomings than most people.
15. At my regular wake-up time I am as energetic as usual.
16. I feel like crying or have trouble controlling my crying.
17. I feel responsible for bad things that have happened.
18. I make decisions as well as I usually do.
19. I often have morbid/negative thoughts and/or think about death or dying.
20. My appetite and/or weight has been stable.

S _____

CORREA – BARRICK SCALE
Clinical Rating for Depression

22 / 21  23
not at all    very much

1. My daily activities are smooth and effortless.
2. I have sleep problems: trouble falling asleep/interrupted sleep/awaken too early/sleeping too much.
3. I look forward to fun things (hobbies/interests/social contact) as much as I usually do.
4. I feel too tired to get through my regular day or need naps more often.
5. My body feels "heavy" (slowed down, sluggish, tired).
6. My concentration is as good as ever.
7. I feel restless/tense/anxious/jittery/wring my hands.
8. I think there is something wrong with my health.
9. My interest in being sensual/physical/loving is the same.
10. I notice that everything seems gray/cloudy/drab/lacking color.
11. I feel depressed (sad, blue, and gloomy).
12. I feel calm/relaxed/easy-going with people.
13. I brood and worry a lot (think about the same thing over and over again).
14. I have more personal faults and shortcomings than most people.
15. At my regular wake-up time I am as energetic as usual.
16. I feel like crying or have trouble controlling my crying.
17. I feel responsible for bad things that have happened.
18. I make decisions as well as I usually do.
19. I often have morbid/negative thoughts and/or think about death or dying.
20. My appetite and/or weight has been stable.

FIG. 1                                    S _____

CORREA - BARRICK SCALE

INSTRUCTIONS FOR SCORING

Begin at each hatch mark (۱) which is always zero points. Each dot scored one (1) point starting from the hatch mark. The slash mark (/) is scored to the nearest half (1/2) point. (See examples below.) Count the total score for the 20 items and enter the total raw score.

*Examples:*

I feel depressed.

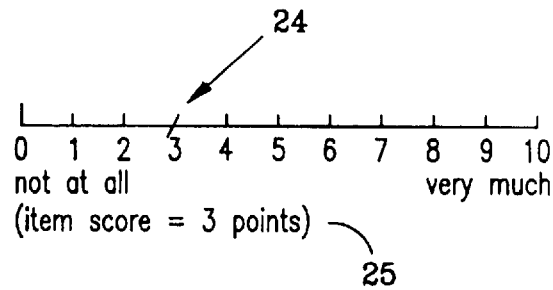

I look forward to fun things as much as I usually do.

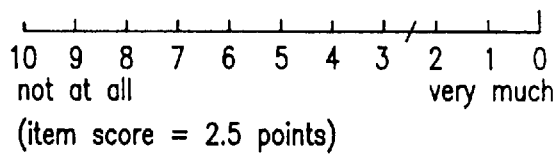

| Total Raw Score | Depression Rating |
|---|---|
| 79 and under | within normal limits |
| 80-90 | dysthymia |
| 100-110 | mild |
| 111-125 | moderate |
| 126 and over | severe |

METHOD OF DETECTING DEPRESSION

FIELD AND BACKGROUND OF INVENTION

This invention relates methods of psychological evaluation, and more particularly to a method of psychological testing that detects depression.

Depression is a prevalent condition that affects more than six million Americans each year. (Weissmian et al., 1988). Depression is a mental disorder involving complex behavioral, psychological, and physiological systems. (DSM-IV). Depression can impair functional capacity, cause distress or increase the risk of suffering pain, disability and death. (DSM-IV) When depression is detected it can be treated with psychotherapy and/or medication.

It is, of course, known in the art to determine characteristics of human test subjects by asking them to select appropriate responses to printed statements, as disclosed in U.S. Pat. No. 4,627,010 issued to Von Fellenberg.

The primary methods for assessing depression include the structured diagnostic interview, the clinician rating scale interview and the self-rating scale method. The structured diagnostic interviews are standardized interviews that specify the questions and inquiries made by raters and the response options for patients. Rabkin and Klein described that clinician rating scales "required the interview to cover specific areas with the client and they provide more or less specific response options." There are difficulties associated with the interview methods. First, the interviewer must be learned in the area of psychlology or psychiatry. Additionally Lambert, Christensen, & DeJulio reported that differences in the interview may result due to the training of the rater, the theoretical base of the rater and the role of the rater. The self-rating scale was designed by Woodworth. A self-rating scale is defined as a procedure for data collection which allows the respondent to report information by placing a response or responses (belief\attitudes\feelings) to an anchor point or points on a survey scale. An advantage of a self-rating scale is that it is effective in initial screening and removing observer bias. (Deforge & Sobal, 1988) Self-rating does not require a skilled interviewer. Finally, self-rating can show changes in the severity of the individual's depression. (Hamilton, 1967)

SUMMARY OF THE INVENTION

The present invention described herein is a method of detecting depression and determining the severity of depression.

The invention exploits the discovery that depression is associated with a decrease in color perception.

The method of the invention is to elicit from a subject an evaluation of the subject's color perception, and changes in that perception. This may be accomplished by interview, by pencil-and-paper questionnaire, by computer-assisted presentation of suitable questions and evaluation of responses, or by passive analysis of data collected which objectively measures a subject's color perception.

An object of this invention is to provide an objective indicator and measure of depression in a human subject.

An object of this invention is to provide an easily administered, easily evaluated, optionally self-rating, depression scale. A further object of this invention is to provide such a scale suitable for paper and pencil administration.

An advantage of this invention is that it can be completed quickly (typically in 10 minutes or less). Another advantage of this invention is that it can be easily scored and interpreted by an interdisciplinary health care team. A further advantage of this invention is its suitability for utilization with a visual analog scale which depressed patients prefer because it is less cognitively taxing. A further advantage of this invention is that it is coded to hinder subject faking.

BRIEF DESCRIPTION OF THE DRAWINGS

The foregoing and still other objects of this invention will become apparent, along with various advantages and features of novelty residing in the present emodiments, from study of the following drawings, in which:

FIG. 1 illustrates a rating scale suitable for use in implementing the invention.

FIG. 2 illustrates a scoring scale suitable for use in implementing the invention.

DETAILED DESCRIPTION OF THE PREFERRED EMBODIMENT

Figure 3:
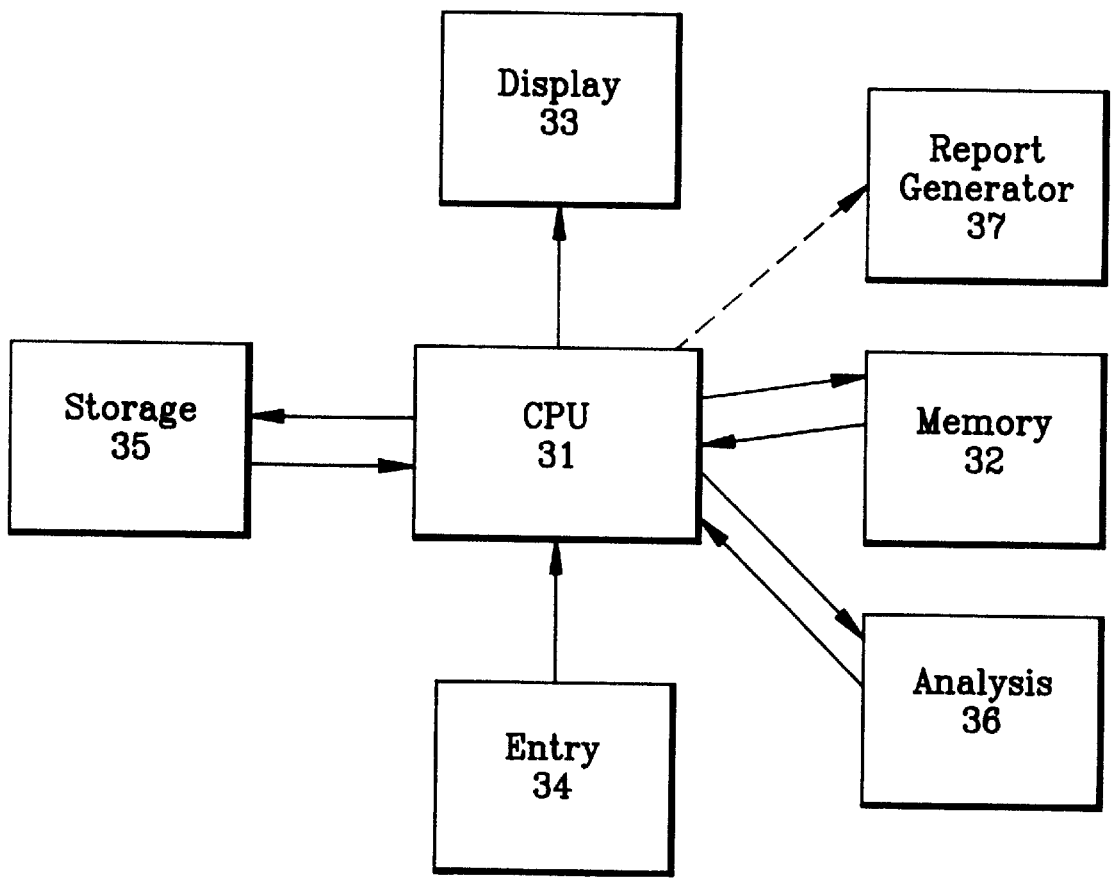
FIG. 3 illustrates a schematic of a computer system suitable for use in implementing the invention.

The invention described herein is for a psychotechnological testing method for detecting the presence and the severity of depression by means of measuring the subject's color perception, and changes in color perception.

The method can be applied to any data which provides a measure of the subject's color perception. It is, however, well-suited to administration in a self-administered and, optionally, self-evaluated test which will be described in detail as the preferred s embodiment of the invention.

A subject is provided with a series of statements, as in FIG. 1, among which is at least one designed to elicit the subject's color perception (FIG. 1, #10), along with an additional series of statements (FIG. 1, #1–9 and 11–20). Optionally, the additiorial statements would be related to other symptoms of depression, a suitable set of such statements including those provided in revised Diagnostic and Statistical Manual of Mental Disorder which are as follows:

1) depressed mood (or can be irritable mood in children and is adolescents) most of the day, nearly every day, as indicated by either subjective account or observation made by others
2) markedly diminished interest or pleasure in all or almost all activities most of the day, nearly every day, as indicated by either subjective report or observation made by others
3) significant weight loss when not dieting or weight gain (e.g., a change of more than 5% of body weight in a month) or decrease or increase in appetite nearly every day (in children consider failure to make expected weight gains)
4) insomnia or hypersomnia nearly every day
5) psychomotor agitation or retardation nearly every day
6) fatigue or loss of energy nearly every day
7) feelings of worthlessness or excessive or inappropriate guilt nearly every day
8) diminished ability to think or concentrate, or indecisiveness, nearly every day
9) recurrent thoughts of death (not just fear of dying), recurrent suicidal ideation without a specific plan, or a suicide attempt or a specific plan for committing suicide.

The set of questions would be presented according to well-known test design criteria, preferably being both negatively and positively phrased to avoid acquiescence bias. For each statement the subject is provided with a visual analog scale (FIG. 1, #21) with diametrically opposed responses written on opposite ends (22, 23) of the scale (21). The scale my be coded. The subject is prompted to mark his level of agreement between the diametrically opposed responses (FIG. 2, #24). The subject's selections are assigned numerical values (FIG. 2, #25). These values are then tabulated. The cut-off scoring to the test is based on normative scores from the population, an example being shown in FIG. 2 (26). The degree of depression the subject is suffering is determined based on his or her score. The psychotechnological testing method scores the range from normal, dysthymia, mild, moderate to severely depressed.

The scale and questions may be presented by pencil-and-paper type questionnaire or could be presented by computer; likewise, scoring could be done manually (either by the subject or an analyst) or by computer. As shown schematically in FIG. 3, a suitable computer would include a central processing unit (31); memory means (32), such as a disk or computer chip, for storing instructions that control the central processing unit, questions or statements designed to elicit information as to the subject's color perception, and response options to each of the questions or statements; display means (33), such as a printer or monitor, connected to the central processing unit for displaying the questions or statements and the response options to the subject; entry means (34), such as a keyboard, mouse, track ball or touchscreen connected to the central processing unit, for enabling the subject to select a response associated with each of the questions or statements; storage means (35), such as a disk, connected to the central processing unit, for recording the subject's response to each question or statement; and analysis means (36), such as computer software stored on a disk and executing in RAM, connected to the central processing unit, for analyzing the subject's responses. optionally, it might also include report generation means (37), such as a printer or monitor, for generating a report of the analysis of the subject's responses.

While specific embodiments of the invention have been shown and described in detail to illustrate the invention, it will be understood that the invention may be embodied otherwise without departing from the principles of the invention and that various rodifications, alternate constructions, and equivalents will occur to those skilled in the art given the benefit of this disclosure, Thus, the invention is not limited to the specific embodiment described herein, but is defined by the appended claims.

We claim:

1. A method of detecting depression in a subject, comprising the steps of:
   obtaining information characterizing the subject's color perception and subjecting the information to psychological interpretation;
   wherein the information is obtained by:
      providing the subject with a multiple-item scale containing a plurality of statements eliciting the subject's color perception and a plurality of statements eliciting other symptoms of depression;
      providing the subject with a visual analog scale with diametrically opposed responses to each statement on opposite ends of the scale for each item;
      prompting the subject to mark his or her level of agreement between the diametrically opposed responses;
      assigning a numerical partial score to each of the selections made by the subject;
      tabulating the subject's total score from numeral values assigned to each selection; and
      determining the degree of depression from the subject's total score based upon normative scoring.

2. A method as in claim 1 wherein the visual analog scale is coded so as to conceal from the subject the numerical value attached to the response.

3. A computer for assessing depression in a subject, comprising:
   a central processing unit;
   memory means for storing: instructions that control the central processing unit, questions or statements designed to elicit information as to the subject's color perception, and response options to each of the questions or statements;
   display means, connected to the central processing unit for displaying the questions or statements and the response options to the subject;
   entry means, connected to the central processing unit, for enabling the subject to select a response associated with each of the questions or statements;
   storage means, connected to the central processing unit, for recording the subject's response to each question or statement; and
   analysis means, connected to the central processing unit, for analyzing the subject's responses.

4. A computer as in claim 3, further comprising report generation means for generating a report of the analysis means relating to the subject's responses.

* * * * *